(12) United States Patent
Benenati

(10) Patent No.: US 9,700,453 B2
(45) Date of Patent: Jul. 11, 2017

(54) ROTATION AND ABDUCTION DEVICE FOR SHOULDER IMMOBILIZATION

(71) Applicant: Vincent A. Benenati, Dix Hills, NY (US)

(72) Inventor: Vincent A. Benenati, Dix Hills, NY (US)

(73) Assignee: Vincent A. Benenati, Dix Hills, NY (US)

( * ) Notice: Subject to any disclaimer, the term of this patent is extended or adjusted under 35 U.S.C. 154(b) by 350 days.

(21) Appl. No.: 13/756,714

(22) Filed: Feb. 1, 2013

(65) Prior Publication Data
US 2014/0221888 A1 Aug. 7, 2014

(51) Int. Cl.
*A61F 5/37* (2006.01)
(52) U.S. Cl.
CPC .................................. *A61F 5/3753* (2013.01)
(58) Field of Classification Search
CPC ........ A61F 5/37; A61F 5/3723; A61F 5/3715; A61F 5/3746
USPC ...... 602/4, 20; 128/845–846, 869, 876, 878; 224/158
See application file for complete search history.

(56) References Cited

U.S. PATENT DOCUMENTS

| 4,836,195 A | * | 6/1989 | Berrehail | A61F 5/3753 602/19 |
| 6,862,870 B1 | * | 3/2005 | Coons | 54/79.2 |
| 8,016,780 B1 | * | 9/2011 | Sickles | A61F 5/3715 602/20 |

* cited by examiner

*Primary Examiner* — Victoria J Hicks
*Assistant Examiner* — Camtu Nguyen
(74) *Attorney, Agent, or Firm* — Curran Patent Law; Kevin M. Curran, Esq.

(57) ABSTRACT

Methods, systems, and apparatus regarding a Rotation & Abduction Device ("RAD") for shoulder immobilization in treating shoulder instability, wherein the ability to maintain particular degrees of shoulder rotation and abduction is desired or necessary. An exemplary RAD shoulder immobilization system may include: a frame; a harness connected to the frame and including a waist support and a neck/shoulder strap; a sling connected to the frame and the harness; and a lining covering parts of the frame, the harness, and/or the sling. A method of treating a shoulder disorder may include: providing a shoulder immobilization system capable of shoulder rotation positioning adjustment and capable of shoulder abduction-adduction positioning adjustment; putting the shoulder immobilization system on a wearer; adjusting the shoulder immobilization system for shoulder rotation positioning; and adjusting the shoulder immobilization system for shoulder abduction-adduction positioning. Numerous other aspects are provided.

18 Claims, 5 Drawing Sheets

20 Degrees of External Rotation:

The RAD Shoulder system in 20 degrees of external rotation.

90 Degrees of Abduction:

The RAD Shoulder system in 90 degrees of abduction.

FIG. 4A

Full Internal Rotation:

The RAD Shoulder system in full internal rotation.

FIG. 4B

10 Degrees of Internal Rotation.

The RAD Shoulder system in 10 degrees of internal rotation.

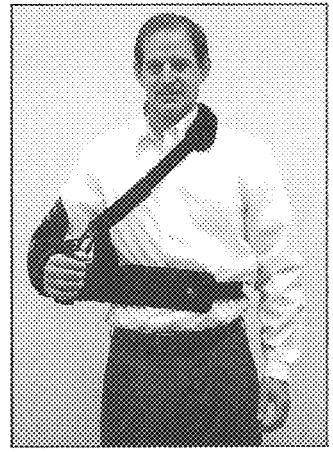

FIG. 4C

Neutral Position:

The RAD Shoulder system in the neutral position.

FIG. 4D

10 Degrees of External Rotation:

The RAD Shoulder system in 10 degrees of external rotation

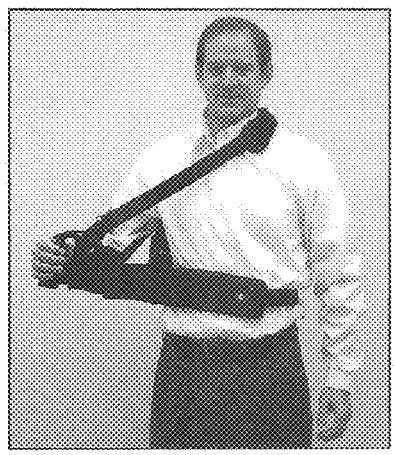

FIG. 4E

20 Degrees of External Rotation:

The RAD Shoulder system in 20 degrees of external rotation.

Adduction:

The RAD Shoulder system in the Adducted position.

15 Degrees of Abduction:

The RAD Shoulder system in 15 degrees of abduction.

30 Degrees of Abduction:

The RAD Shoulder system in 30 degrees of abduction.

45 Degrees of Abduction:

The RAD Shoulder system in 45 degrees of abduction.

90 Degrees of Abduction:

The RAD Shoulder system in 90 degrees of abduction.

ROTATION AND ABDUCTION DEVICE FOR SHOULDER IMMOBILIZATION

CROSS REFERENCE TO RELATED APPLICATION

This application is related to and claims the benefit of U.S. Provisional Patent Application Ser. No. 61/489,400 ("the '400 application"), titled "Rotation And Abduction Device For Shoulder Immobilization," and filed Feb. 2, 2012, which is incorporated by reference herein in its entirety for all purposes.

BACKGROUND OF THE INVENTION

Field of the Invention

The invention relates to systems, methods and apparatus of restricting movement of body parts, including braces for immobilization of limbs. In particular, the invention relates to a Rotation & Abduction Device ("RAD") for shoulder immobilization.

Description of Related Art

The related art includes, for instance, braces for immobilization of shoulders for wearers who have had shoulder surgery, who have injured a shoulder, or who otherwise require restriction of shoulder movement. For instance, prior art shoulder braces include embodiments known as a "gunslinger" brace and an "airplane" brace. However, prior art braces commonly restrict positioning of one type or direction. Moreover, prior art braces are not capable of large adjustment of shoulder rotation positioning as well as large adjustment of shoulder abduction-adduction positioning. For example, the Abduction Rotation Control ("ARC") Shoulder Brace from Bledsoe Brace Systems allows minimal adjustment of abduction, ranging from adduction to about 5 to 10 degrees of abduction, and minimal adjustment of rotation, ranging between up to 15 degrees of internal rotation and up to 15 degrees of external rotation. Patients needing external rotation beyond 15 degrees are directed to use Bledsoe's ARC-XR brace. Although the ARC-XR brace allows for increased external rotation, it still does not allow increased abduction adjustment. Conversely, prior art Quadrant® "airplane" braces have abduction hinges to fix abduction positioning, but without fixing, or even sometimes restricting, rotation. Likewise, Acro Assist Arm Abduction Orthosis 50A1 enables functional shoulder positioning with arm abduction at 30, 60, or 90 degrees, but does not provide shoulder rotation positioning adjustment. As such, the prior art uses multiple braces to achieve multiple positions, often using a particular brace to achieve a particular position.

BRIEF SUMMARY OF THE INVENTION

The invention is directed to methods, systems, and apparatus involving shoulder immobilization using a shoulder immobilization system providing shoulder rotation positioning as well as shoulder abduction-adduction positioning. Shoulder rotation positioning may go from about 20 degrees of inward rotation (full internal rotation) up to about 45 degrees of outward rotation (full external rotation). Shoulder abduction-adduction positioning may go from neutral (adduction) up to about 90 degrees of abduction. The shoulder immobilization system may be used in cases of, for instance, arthroscopy, rotator cuff surgery, labral repairs, total shoulder repair, and other shoulder injuries. Moreover, the invention is also effective in treating shoulder instability repairs wherein the ability to maintain a particular degree of external rotation is desired or necessary.

In accordance with a first aspect of the invention, a method of treating a shoulder disorder is disclosed, wherein the method comprises: providing a shoulder immobilization system capable of shoulder rotation positioning adjustment and capable of shoulder abduction-adduction positioning adjustment; putting the shoulder immobilization system on a wearer; adjusting the shoulder immobilization system for shoulder rotation positioning; and adjusting the shoulder immobilization system for shoulder abduction-adduction positioning.

In accordance with a second aspect of the invention, a shoulder immobilization system is disclosed, wherein the system comprises: a frame; a harness connected to the frame and including a waist support and a neck/shoulder strap; a sling connected to the frame and the harness; and a lining covering parts of the frame, the harness, and/or the sling.

The details of exemplary embodiment of the invention are set forth in the accompanying drawings and the description below. Other features, objects, and advantages of the invention will be apparent from the description and drawings, and from the claims.

BRIEF DESCRIPTION OF THE DRAWINGS

By reference to the appended drawings, which illustrate an exemplary embodiment of this invention, the detailed description provided below explains in detail various features, advantages and aspects of this invention. As such, features of this invention can be more clearly understood from the following detailed description considered in conjunction with the following drawings, in which the same reference numerals denote the same elements throughout. The exemplary embodiment illustrated in the drawings is not necessarily to scale and is not to be considered limiting of its scope, for the invention may admit to other equally effective embodiments.

FIGS. 4A-4E show front elevation view images of a wearer wearing an exemplary shoulder immobilization system at varying positions of shoulder rotation, according to aspects of the invention.

DETAILED DESCRIPTION

Figure 1:
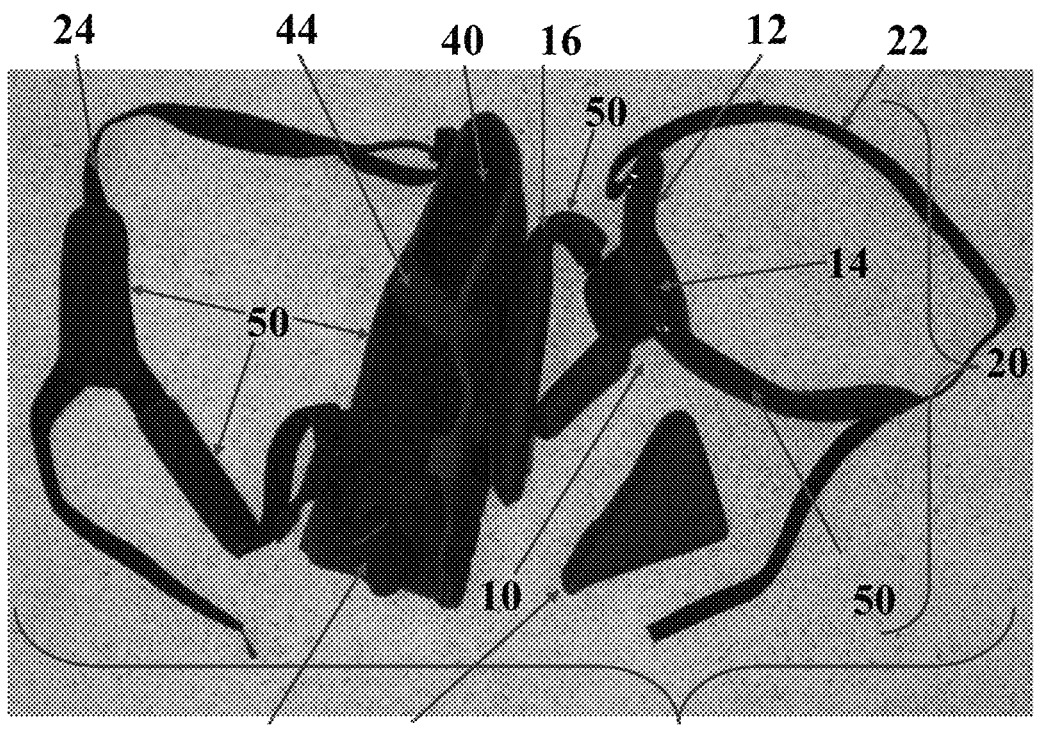
FIG. 1 shows a plan view image of an exemplary embodiment of the invention.
Figure 2:
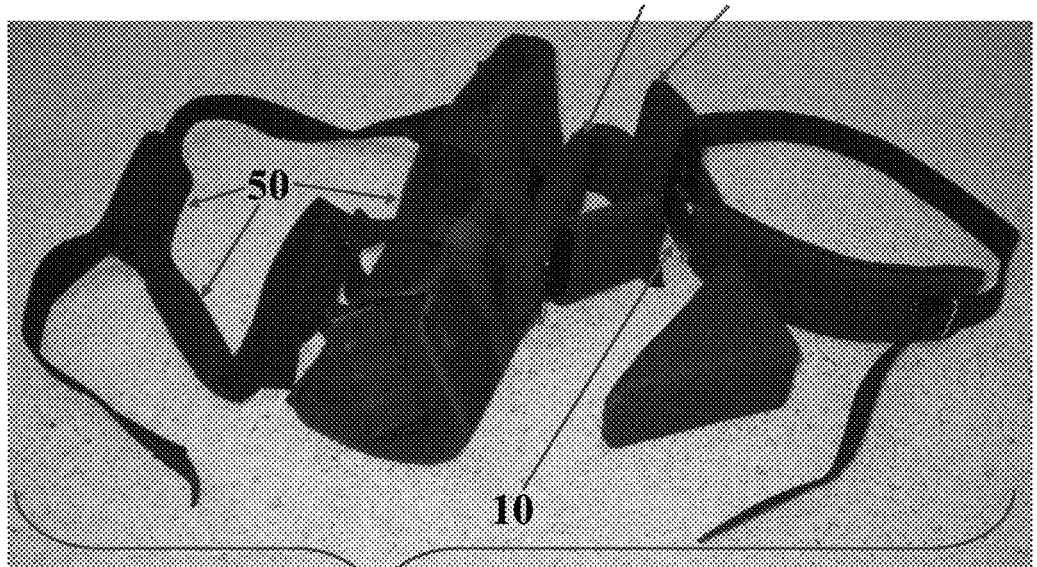
FIG. 2 shows a front perspective view image of an exemplary embodiment of FIG. 1.
Figure 3A:
FIGS. 3A and 3B show side perspective views, body in front of arm and arm in front of body, respectively, of the exemplary embodiment of FIG. 1.
Figure 3B:

As shown in FIG. 1, an exemplary RAD shoulder immobilization system 100 according to the invention may include, for example: a frame 10; a harness 20 connected to the frame and including a waist strap 22 and a neck/shoulder strap 24; a support block 30; a sling 40 connected to the frame 10 and the harness 20; and a lining 50 covering parts of the frame 10, the harness 20, the support block 30, and/or the sling 40. These components are shown from different angles in FIGS. 2, 3A, and 3B. FIG. 2 shows a front perspective view image of an exemplary embodiment of FIG. 1, whereas FIGS. 3A and 3B show side perspective views, body in front of arm and arm in front of body, respectively, of the exemplary embodiment of FIG. 1.

The frame 10 may include an assembly of pieces made, for instance, of metal, wood, or hard, durable plastic. The assembly may include a waist piece 12 or hip piece that distributes weight and creates resistance against the hip or waist of the wearer. The waist piece 12 may be pliable to conform to a wearer's shape. For instance, a metal waist piece 12 may be bent to conform to a wearer's shape, and be resilient enough to maintain that bend under normal wearing conditions, but also be forgiving enough to bend without breaking if subjected to excess force, such as during a fall of the wearer. If bent under excess force, a metal waist piece 12 may be re-shaped by applying force in the necessary direction. The waist piece 12 may be covered by the lining 50 to buffer the wearer from the frame 10. The waist piece 12 also may be attached to the waist strap 22 of the harness 20. The waist strap 22 may begin from a back side of the waist piece 12, go around the wearer's waist, and tighten onto to a front side of the waist piece 12, using any means, but preferably those that are detachable and re-attachable, such as by hook, carabiner, hook-and-loop fasteners, buckles, snaps, knots, buttons, or strap loops, etc. The waist strap 22, and any other disclosed strap, may be made, for instance, of durable nylon, polyester, rayon, cotton, leather, pliable resin, pliable rubber, woven fabric, etc. The waist strap 22, as well as any other disclosed strap, may be adjustable and/or elastic to accommodate different sizes of wearers or different layers/thicknesses of clothing for a single wearer.

Attached to the waist piece 12 is an abduction support piece 14 that positions and supports the arm in the desired adduction-abduction position. The abduction support piece 14 may be adjustable to allow for varying degrees of abduction from a single brace. Adjustability may take the form, for example, of a geared hinge, a ratchet, a locking hinge, or a pliable bend 15 in material (e.g., a resilient but bendable piece of metal). For instance, a metal abduction support piece 14 may be bent to conform to a wearer's needed abduction, and be resilient enough to maintain that bend under normal wearing conditions, but also be forgiving enough to bend without breaking if subjected to excess force, such as during a fall of the wearer. If bent under excess force, a metal abduction support piece 14 may be re-shaped by applying force in the necessary direction. Alternatively, the abduction support piece 14 may be fixed but exchangeable to allow adjust for desired abduction positioning by choosing a piece having a corresponding angle of abduction. The abduction support piece 14 may be covered in lining 50 to buffer the wearer from the rigid support piece.

Attached to the abduction support piece 14 is a forearm support piece 16 that extends along, supports and rests against the forearm. The forearm support piece 16 preferably is rigid and long enough to immobilize the forearm, which in turn maintains a specific degree of rotation of the shoulder. The forearm support piece 16 may be adjustable to allow for varying degrees of rotation from a single brace. Adjustability may take the form, for example, of a geared hinge, a ratchet, a locking hinge, or a pliable bend 17 in material (e.g., a resilient but bendable piece of metal). For instance, a metal forearm support piece 16 may be straight to conform to a wearer's forearm, and be resilient enough to maintain that straightness under normal wearing conditions, but also be forgiving enough to bend without breaking if subjected to excess force, such as during a fall of the wearer. If bent under excess force, a metal forearm support piece 16 may be re-straightened by applying force in the necessary direction. Alternatively, the forearm support piece may be fixed but exchangeable to allow adjust for desired rotation positioning by choosing a piece having a corresponding angle of rotation. The forearm support piece 16 may be covered in lining 50 to buffer the sling and the wearer from the rigid support piece.

Depending on the angles of rotation and/or abduction selected for immobilization of a wearer's shoulder, use of the support block 30 may be desirable, such as to support the abduction support piece 14 or the forearm support piece 16. The support block 30 may be covered in lining 50 and may comprise, for example, rigid foam, pliable foam, or padding, etc., depending on how much support is desired.

Outward from, and attached to, the forearm support piece 16 is the sling 40, into which the forearm is placed, and by which the forearm is held in place. The sling 40 may include a handle grip 42 at a hand opening for a wearer to hold. The sling 40 may include one or more sling straps 44 to tighten the sling 40 on the forearm. The sling straps 44 also may connect to the harness 20, such as to the neck/shoulder strap 24. The neck/shoulder strap 24 may begin from a back side of the sling 40, go around the wearer's back, neck and opposite shoulder, and tighten onto to a front side of the sling 40 using any means, but preferably those that are detachable and re-attachable, such as by hook, carabiner, hook-and-loop fasteners, buckles, snaps, knots, buttons, or strap loops, etc. The sling 40 may be attached to the forearm support piece 16 using any means, but preferably those that are detachable and re-attachable, including hook, carabiner, hook-and-loop fasteners, buckles, snaps, knots, buttons, or strap loops, etc. In the embodiment of shown in FIGS. 1-3, for example, the sling 40 is attached to the forearm support piece 16 using a strong hook-and-loop attachment means that allows adjustment of the sling 40 along the forearm support piece 16. The sling 40 may be made of the same or similar materials used to make the lining 50, such as nylon, cotton, polyester, neoprene, rayon, leather, etc. The sling 40 and/or the lining 50 also may include padding, such as made of foam or quilted fabric, for comfort and shock absorption.

As discussed more below, an exemplary method of treating a shoulder disorder is disclosed, wherein the method comprises: providing a shoulder immobilization system capable of shoulder rotation positioning adjustment and capable of shoulder abduction-adduction positioning adjustment; putting the shoulder immobilization system on a wearer; adjusting the shoulder immobilization system for shoulder rotation positioning; and adjusting the shoulder immobilization system for shoulder abduction-adduction positioning.

Described herein are several specific examples of embodiments in accordance with the invention. The examples are not intended to limit the scope of the invention, which is defined by the claims issuing herefrom.

Exemplary Treatment Using Shoulder Rotation

Referring to FIGS. 4A-4E, front elevation view images depict a wearer wearing an exemplary shoulder immobilization system at varying positions of shoulder rotation, according to aspects of the invention. The images depict results of a method of stabilizing a shoulder, the method comprising: providing a shoulder immobilization system capable of shoulder rotation positioning adjustment and capable of shoulder abduction-adduction positioning adjustment; putting the shoulder immobilization system on a wearer; and adjusting the shoulder immobilization system for shoulder rotation positioning. FIG. 4A shows the system in full internal rotation, wherein the shoulder is rotated about 20 degrees inward from a neutral rotation position. FIG. 4B shows the system in partial internal rotation, wherein the shoulder is rotated about 10 degrees inward from the neutral rotation position. FIG. 4C shows the system in the neutral rotation position, wherein the shoulder is rotated about 0 degrees inward or outward. FIG. 4D shows the system in partial external rotation, wherein the shoulder is rotated about 10 degrees outward from the neutral rotation position. FIG. 4E shows the system in greater external rotation, wherein the shoulder is rotated about 20 degrees outward from the neutral rotation position.

Exemplary Treatment Using Shoulder Adduction and Abduction

Figure 5A:
FIGS. 5A-5E show front elevation view images of a wearer wearing an exemplary shoulder immobilization system at varying positions of shoulder adduction and abduction, according to aspects of the invention.
Figure 5B:
Figure 5C:
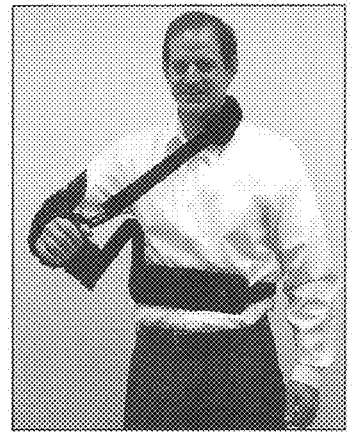
Figure 5D:
Figure 5E:
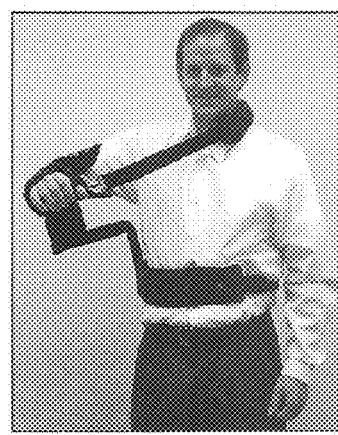

Referring to FIGS. 5A-5E, front elevation view images depict a wearer wearing an exemplary shoulder immobilization system at varying positions of shoulder adduction and abduction, according to aspects of the invention. The images depict results of a method of stabilizing a shoulder, the method comprising: providing a shoulder immobilization system capable of shoulder rotation positioning adjustment and capable of shoulder abduction-adduction positioning adjustment; putting the shoulder immobilization system on a wearer; and adjusting the shoulder immobilization system for shoulder abduction-adduction positioning. FIG. 5A shows the system in full adduction, wherein the shoulder is abducted about 0 degrees upward or outward from a neutral abduction position. FIG. 5B shows the system in partial upward abduction, wherein the shoulder is abducted about 15 degrees upward and outward from the neutral abduction position. FIG. 5C shows the system in a greater abduction position, wherein the shoulder is abducted about 30 degrees upward. FIG. 5D shows the system in middle upward abduction, wherein the shoulder is abducted about 45 degrees upward from the neutral abduction position. FIG. 5E shows the system in still greater external abduction, wherein the shoulder is abducted about 90 degrees upward from the neutral abduction position. The degrees of abduction may be made determined by the extent to which the abduction support piece 14 is splayed.

Various exemplary RAD shoulder immobilization system embodiments are possible in accordance with the invention. Numerous applications of these embodiments are contemplated as well. For example, exemplary RAD shoulder immobilization system embodiments in accordance with the invention may be used as treatments of, for instance, arthroscopy, rotator cuff surgery, labral repairs, total shoulder repair, and other shoulder injuries. Moreover, the invention is also effective in treating shoulder instability repairs where the ability to maintain a particular degree of external rotation is desired or necessary.

The foregoing description discloses exemplary embodiments of the invention. While the invention herein disclosed has been described by means of specific embodiments and applications thereof, numerous modifications and variations could be made thereto by those skilled in the art without departing from the scope of the invention set forth in the claims. Modifications of the above disclosed apparatus and methods that fall within the scope of the invention will be readily apparent to those of ordinary skill in the art. Accordingly, other embodiments may fall within the spirit and scope of the invention, as defined by the following claims.

In the description above, numerous specific details are set forth in order to provide a more thorough understanding of embodiments of the invention. It will be apparent, however, to an artisan of ordinary skill that the invention may be practiced without incorporating all aspects of the specific details described herein. In other instances, specific details well known to those of ordinary skill in the art have not been described in detail so as not to obscure the invention.

Readers should note that although examples of the invention are set forth herein, the claims, and the full scope of any equivalents, are what define the metes and bounds of the invention.

What is claimed is:

1. A method of stabilizing a shoulder, the method comprising:
providing a shoulder immobilization system capable of shoulder rotation positioning adjustment and capable of shoulder abduction-adduction positioning adjustment, wherein each of the shoulder rotation positioning adjustment and the shoulder abduction-adduction positioning adjustment applies direct support only to a forearm of a wearer; wherein the shoulder immobilization system comprises an abduction support piece that is adjustable to allow for varying degrees of abduction to enable the shoulder abduction-adduction positioning adjustment, is integral to the shoulder immobilization system, and is capable of resilient-but-changeable adjustments;
putting the shoulder immobilization system on the wearer; and
adjusting the shoulder immobilization system for the wearer;
wherein the shoulder immobilization system further comprises a forearm support piece and a waist piece;
wherein the abduction support piece comprises a first rigid support piece having a waist piece attachment portion, a forearm support piece attachment portion, and an adjustable angled abduction portion between the waist piece attachment portion and the forearm support piece attachment portion; with the waist piece attachment portion attached to and extending upward from the waist piece toward the adjustable angled abduction portion, the forearm support piece attachment portion attached to and extending upward from the forearm support piece toward the adjustable angled abduction portion, and the adjustable angled abduction portion adjustable and resiliently maintaining an angle of abduction separating the forearm support piece attachment portion from the waist piece attachment portion; and
wherein the forearm support piece comprises a second rigid support piece having an abduction support piece attachment portion, a forearm support portion, and an adjustable angled rotation portion between the abduction support piece attachment portion and the forearm support portion; with the abduction support piece attachment portion attached to the forearm support piece attachment portion and extending backward from the abduction support piece toward the adjustable angled rotation portion, the forearm support portion extending backward toward the adjustable angled rotation portion, and the adjustable angled rotation adjustable and resiliently maintaining an angle or rotation separating the forearm support portion from the abduction support piece attachment portion.

2. The method of claim 1, wherein:
adjusting the shoulder immobilization system comprises adjusting the shoulder immobilization system for shoulder rotation positioning.

3. The method of claim 1, wherein:
adjusting the shoulder immobilization system comprises adjusting the shoulder immobilization system for shoulder abduction-adduction positioning.

4. The method of claim 1, wherein the adjustable angled abduction portion comprises a first pliable bend in material, and wherein the adjustable angled rotation portion comprises a second pliable bend in material.

5. The method of claim 1, wherein:
shoulder abduction-adduction positioning adjustment ranges from a neutral adduction position up to about 90 degrees of abduction.

6. The method of claim 1, wherein:
shoulder rotation positioning adjustment ranges from about 20 degrees of internal rotation up to about 45 degrees of external rotation.

7. The method of claim 1, wherein:
shoulder rotation positioning adjustment ranges from about 20 degrees of internal rotation up to about 45 degrees of external rotation; and
shoulder abduction-adduction positioning adjustment ranges from a neutral adduction position up to about 90 degrees of abduction.

8. The method of claim 1, wherein the shoulder immobilization system comprises:
a frame;
a harness connected to the frame; and
a sling connected to the frame and the harness;
wherein the frame includes a waist piece, an abduction support piece attached to the waist piece, and a forearm support piece attached to the abduction support piece.

9. The method of claim 8, wherein the shoulder immobilization system further comprises:
a lining covering parts of the frame, the harness, and/or the sling;
a waist support; and
a neck/shoulder strap.

10. The method of claim 9, wherein:
the frame comprises metal pliable enough for shaping and resilient enough to maintain shape during normal wear.

11. The method of claim 9, wherein the shoulder immobilization system further comprises:
an attachment means to connect the sling to the frame, wherein the attachment means is detachable for positioning and attachable resiliently enough to maintain position during normal wear.

12. A shoulder immobilization system comprising:
a frame;
a harness connected to the frame; and
a sling connected to the frame and the harness;
wherein the frame includes a waist piece, an abduction support piece attached to the waist piece, and a forearm support piece attached to the abduction support piece,
wherein the shoulder immobilization system is capable of shoulder rotation positioning adjustment and capable of shoulder abduction-adduction positioning adjustment, and wherein the abduction support piece is adjustable to allow for varying degrees of abduction to enable the shoulder abduction-adduction positioning adjustment, is integral to the shoulder immobilization system, and is capable of resilient-but-changeable adjustments,
wherein each of the shoulder rotation positioning adjustment and the shoulder abduction-adduction positioning adjustment applies direct support only to a forearm of a wearer,
wherein the abduction support piece comprises a first rigid support piece having a waist piece attachment portion, a forearm support piece attachment portion, and an adjustable angled abduction portion between the waist piece attachment portion and the forearm support piece attachment portion; with the waist piece attachment portion attached to and extending upward from the waist piece toward the adjustable angled abduction portion, the forearm support piece attachment portion attached to and extending upward from the forearm support piece toward the adjustable angled abduction portion, and the adjustable angled abduction portion adjustable and resiliently maintaining an angle of abduction separating the forearm support piece attachment portion from the waist piece attachment portion; and
wherein the forearm support piece comprises a second rigid support piece having an abduction support piece attachment portion, a forearm support portion, and an adjustable angled rotation portion between the abduction support piece attachment portion and the forearm support portion; with the abduction support piece attachment portion attached to the forearm support piece attachment portion and extending backward from the abduction support piece toward the adjustable angled rotation portion, the forearm support portion extending backward toward the adjustable angled rotation portion, and the adjustable angled rotation adjustable and resiliently maintaining an angle or rotation separating the forearm support portion from the abduction support piece attachment portion.

13. The shoulder immobilization system of claim 12, wherein:
shoulder rotation positioning adjustment ranges from about 20 degrees of internal rotation up to about 45 degrees of external rotation.

14. The shoulder immobilization system of claim 12, wherein:
shoulder abduction-adduction positioning adjustment ranges from a neutral adduction position up to about 90 degrees of abduction.

15. The shoulder immobilization system of claim 12, wherein the adjustable angled abduction portion comprises a first pliable bend in material, and wherein the adjustable angled rotation portion comprises a second pliable bend in material.

16. The shoulder immobilization system of claim 12, further comprising:
a lining covering parts of the frame and/or the harness;
a waist support; and
a neck/shoulder strap.

17. The shoulder immobilization system of claim 16, wherein:
the frame comprises metal pliable enough for shaping and resilient enough to maintain shape during normal wear.

18. The shoulder immobilization system of claim 16, further comprising:
means for attaching the sling to the frame, wherein the means for attaching is detachable for positioning and attachable resiliently enough to maintain position during normal wear.

* * * * *

UNITED STATES PATENT AND TRADEMARK OFFICE
CERTIFICATE OF CORRECTION

PATENT NO. : 9,700,453 B2
APPLICATION NO. : 13/756714
DATED : July 11, 2017
INVENTOR(S) : Vincent A. Benenati It is certified that error appears in the above-identified patent and that said Letters Patent is hereby corrected as shown below:

On the Title Page

After the text on Lines 16-17:
"(65) Prior Publication Data
US 2014/0221888 A1 Aug. 7, 2014"
Insert the following:
-- Related U.S. Application Data
(60) Provisional application No. 61/594,349, filed on Feb. 2, 2012. --

Signed and Sealed this
Third Day of May, 2022

Katherine Kelly Vidal
*Director of the United States Patent and Trademark Office*